United States Patent [19]

Nieman

[11] Patent Number: 5,047,135
[45] Date of Patent: Sep. 10, 1991

[54] ELECTROPHORESIS APPARATUS

[76] Inventor: Erik Nieman, 201 Monticchio, 251 Jacob Mare Street, Pretoria, South Africa

[21] Appl. No.: 327,269

[22] Filed: Mar. 22, 1989

[30] Foreign Application Priority Data

Mar. 22, 1988 [ZA] South Africa .................. 88/2019

[51] Int. Cl.⁵ ............................................ G01N 27/26
[52] U.S. Cl. .............................. 204/299 R; 204/180.1; 204/182.8
[58] Field of Search .............. 204/180.1, 182.8, 299 R

[56] References Cited

U.S. PATENT DOCUMENTS 3,888,758  6/1975  Saeed ........................... 204/299 R
4,844,787  7/1989  Akao et al. ................... 204/299 R Primary Examiner—T. Tung
Assistant Examiner—David G. Ryser
Attorney, Agent, or Firm—Millen, White & Zelano

[57] ABSTRACT

A gel electrophoresis system is provided in which the slab gel, which we term a multi-gel slab gel, is subdivided by means of thin divider sheets into wafer-like micro-gels. This composite slab gel is electrophoresed as a single slab gel, but after the electrophoresis run the micro-gels may be peeled off and separately processed. Also provided is a divider means for constructing a multi-gel container means for casting the multi-gel slab gel therein.

52 Claims, 6 Drawing Sheets

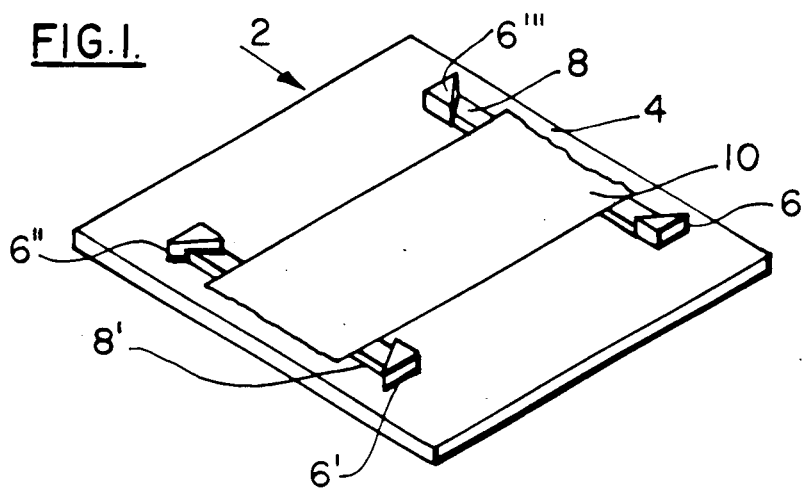
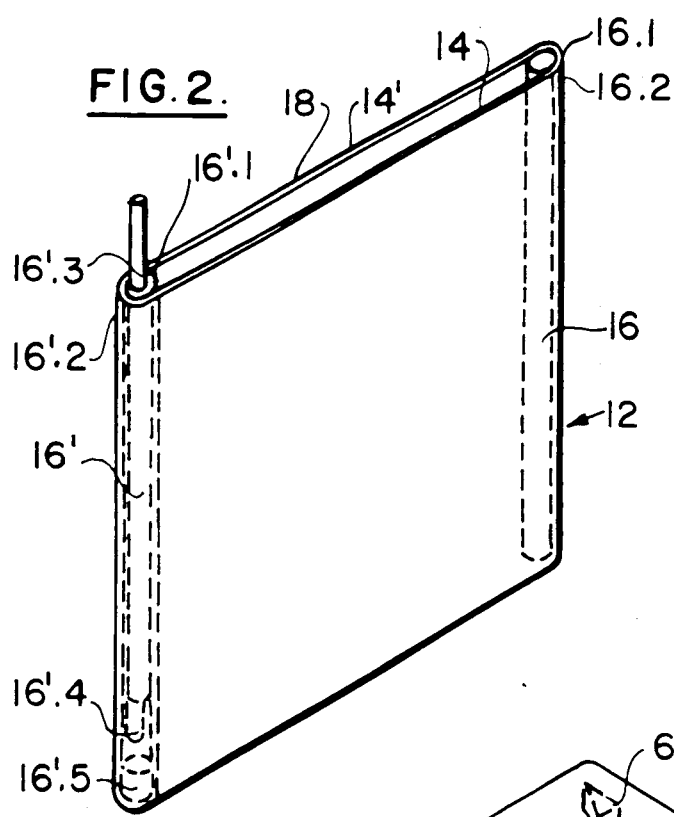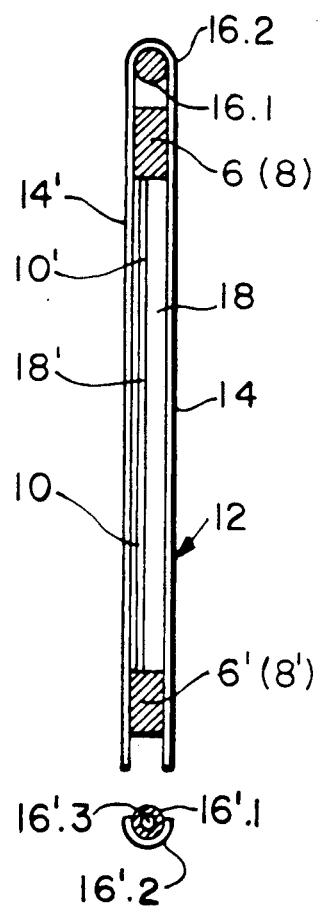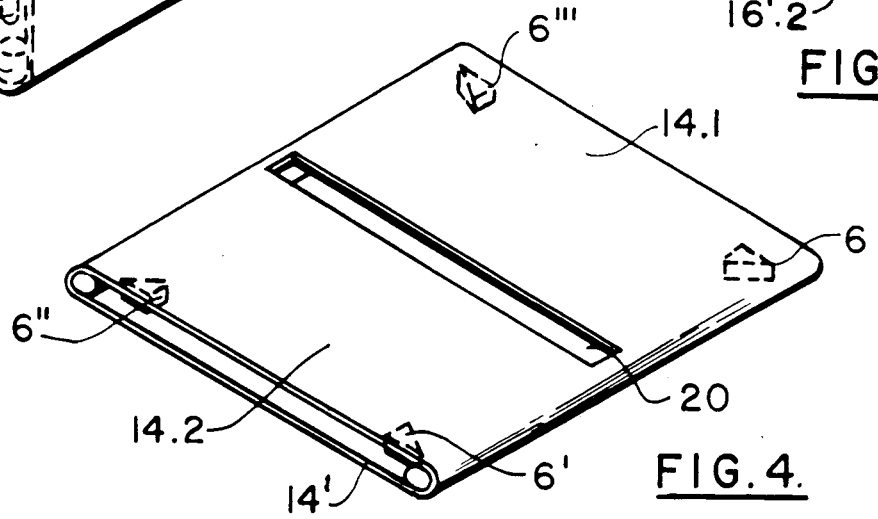

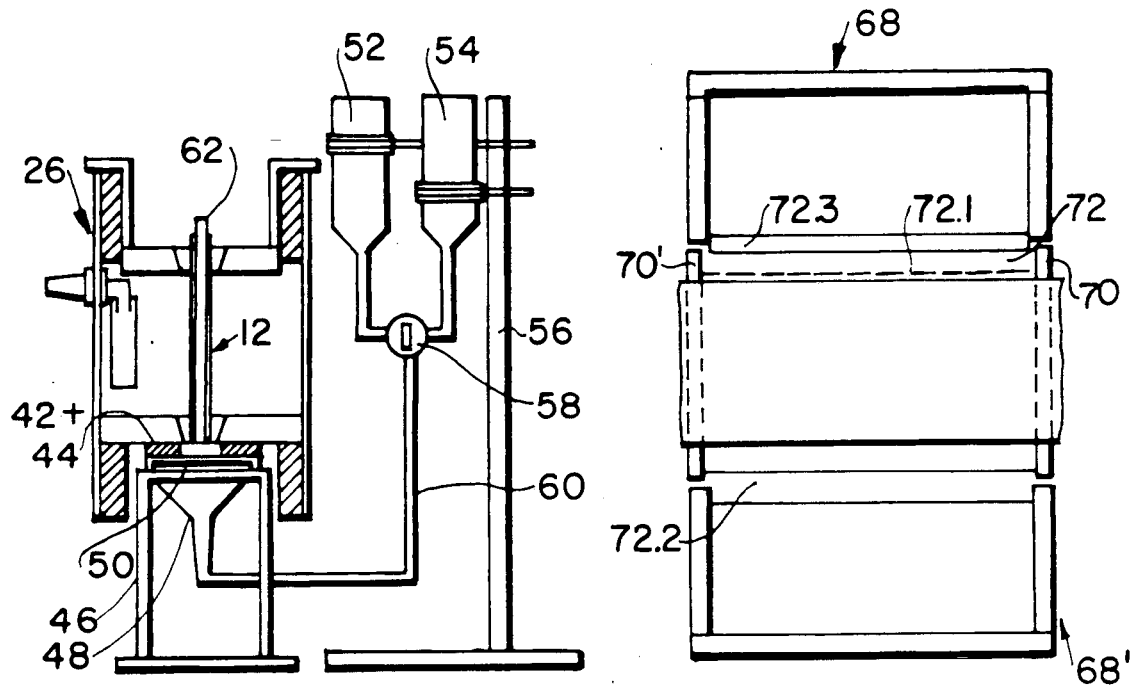
FIG. 13.
FIG. 16.
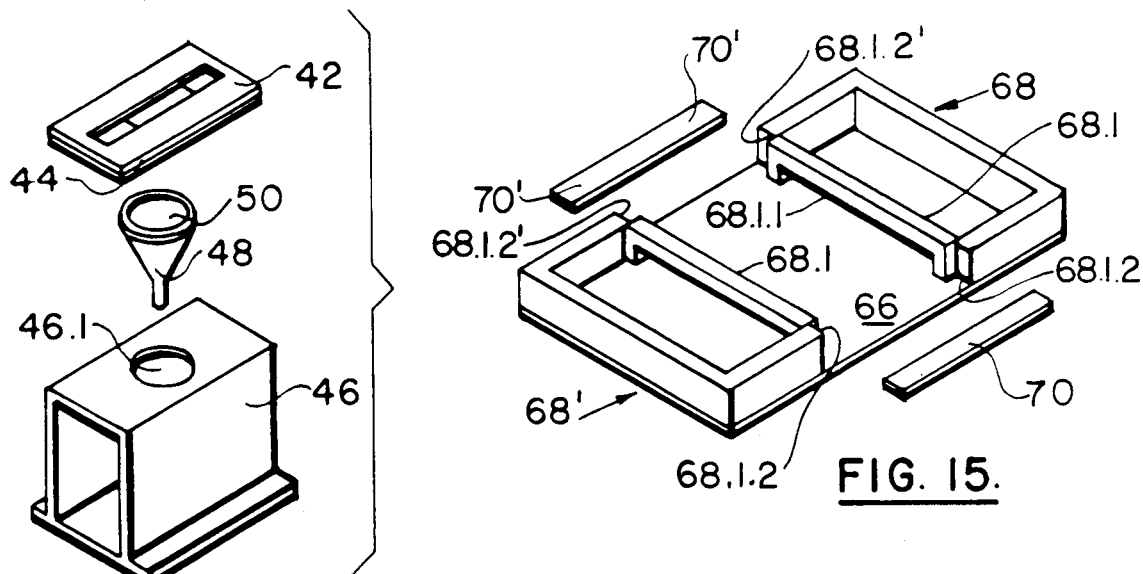
FIG. 14.
FIG. 15.
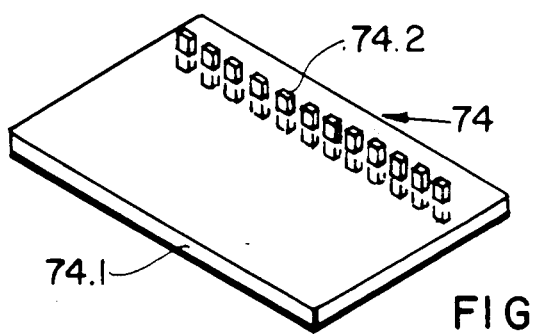
FIG. 17.

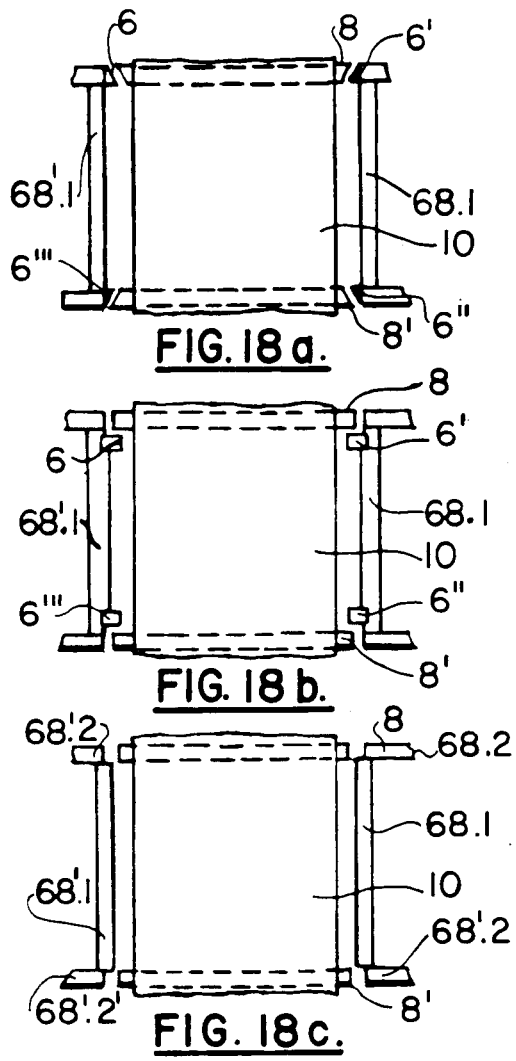
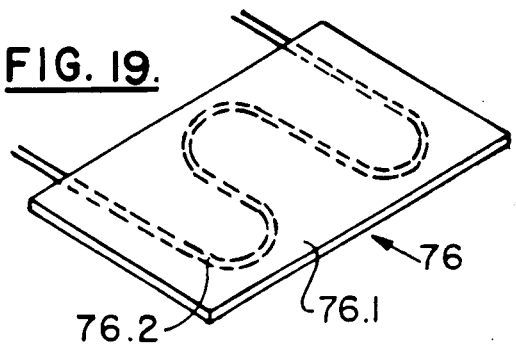
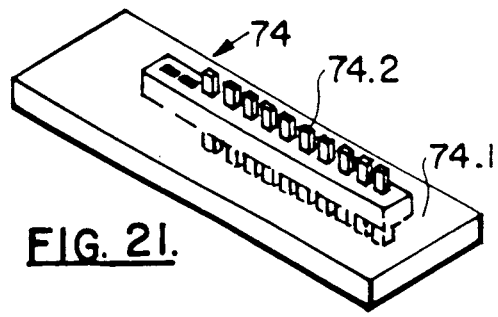
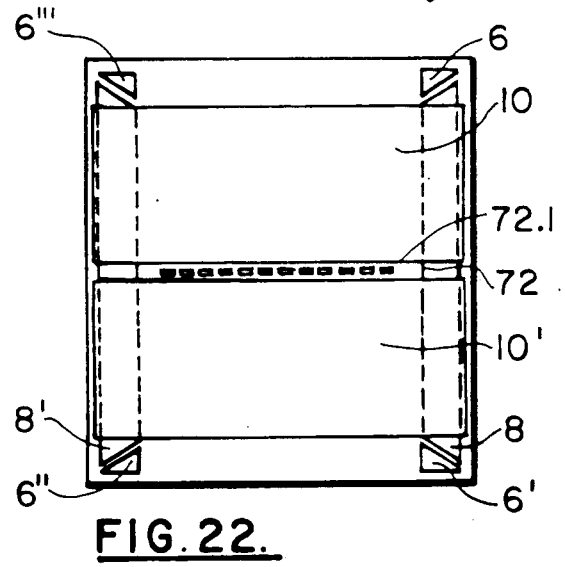
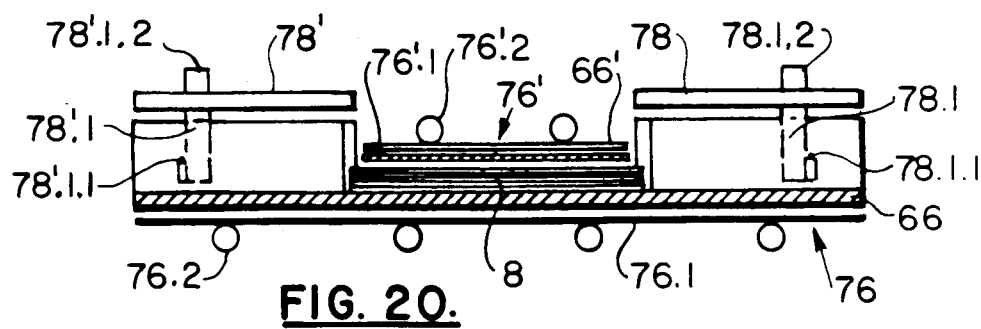

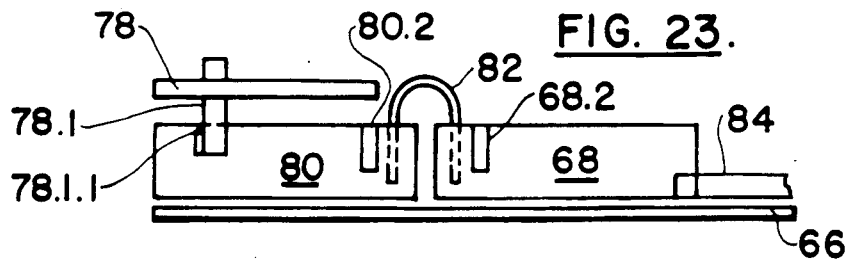
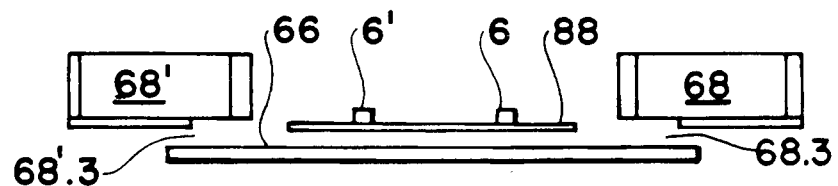
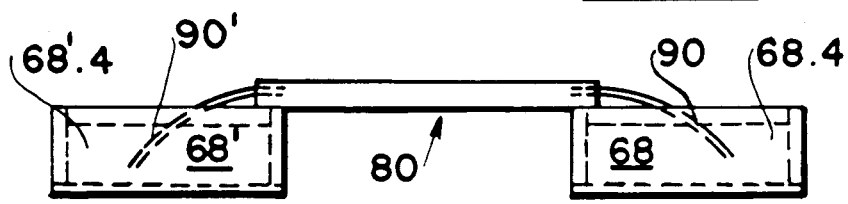
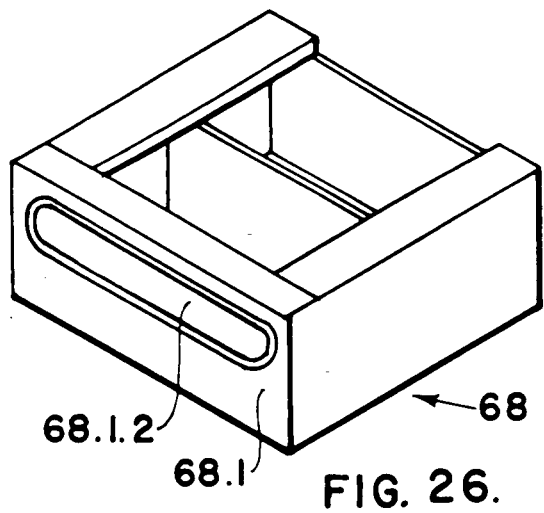
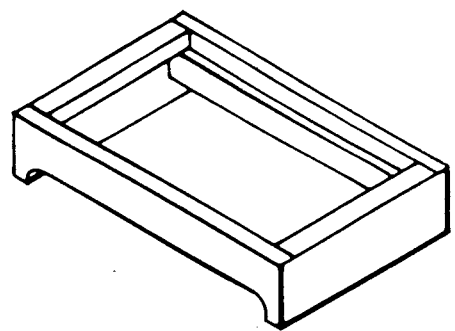
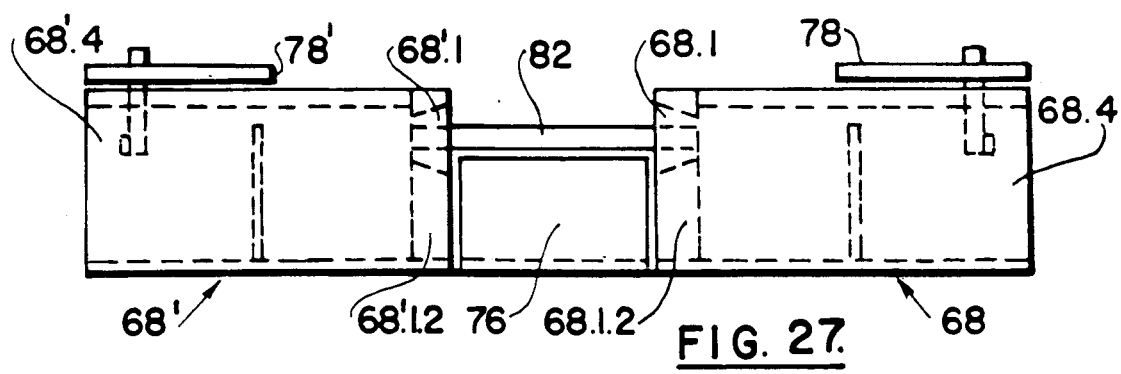

ELECTROPHORESIS APPARATUS

BACKGROUND TO THE INVENTION

The present invention relates to improvements in electrophoresis apparatus. More particularly it relates to improvements in apparatus for both vertical and horizontal (or so-called flat-bed) electrophoresis.

Electrophoresis, an analytical separation and analysis technique, has become an indispensible tool in science, particularly in the analysis of biological samples for enzymes, proteins, DNA, RNA and even chromosomes. Many variations of the technique have been developed over the past two decades, including slab and tube gel electrophoresis, and gradient and electrofocusing electrophoresis, and equipment for these purposes are available commercially from several suppliers. In recent years the paper and starch matrices used earlier have been largely superseded by synthetic polymer gel matrices, including polyacrylamide, and agarose gels. Polyacrylamide gels have become particularly popular, largely because of their superior resolution ability, to the extent that this type of gel has been effectively adopted as a universal standard. Because acrylamide is a synthetic compound the gel may be made up quickly and with good reproducibility, and the porosity of the gel may be varied controllably by varying the proportions of the polymer and a co-polymer, N,N'-methylene-bis-acrylamide, known popularly as "Bis".

However, analytical PAGE (the acronym generally used for polyacrylamide electrophoresis) and the commercially available apparatus for its performance suffer from a number of disadvantages. Firstly, acrylamide is claimed to be a neurotoxin and thus requires special precaution in its handling. Secondly, polyacrylamide slab gels, as well as agarose gels unlike starch slab gels, cannot readily be cut (or sliced) into thinner slabs after polymerisation has taken place and a set of samples has been run.

As a result, when a relatively large number of proteins and/or enzymes, etc. have to be analyzed for in the same sample (or set of samples) by PAGE, repetitive electrophoretic separations may have to be performed. This may not always be possible when the available sample(s) is/are very small. Moreover, complications may arise from the fact that the attainment of reproducible separations in successive runs with aliquots of the same sample(s) is not always easy.

Most of the equipment available in the trade permits the running of only a single slab gel at a time, although apparatus has become available in the last few years that permits the simultaneous running of a pair or even several slab gels, but then in a combination of separate cells. For these combinations, if the gels are connected in series, provision has to be made for high-voltage power units providing rather high potential differences, and if connected in parallel, the power units must be capable of delivering rather large currents. These high voltages and currents in turn aggravate the risk of shocks for the operator.

Since electrophoresis is a time-consuming analytical method, typically requiring several hours to complete a run, it would be advantageously simultaneously to produce a plurality of symograms (also termed electrophoretograms) from a single set of samples, preferably under identical experimental conditions.

BRIEF SUMMARY OF THE INVENTION

An object of the present invention is to provide a means for simultaneously producing several zymograms by electrophoresis of a single sample (or set of samples), preferably by both vertical and horizontal electrophoresis. A further object of the invention is to provide improvements in slab gels for electrophoresis, to permit an economy in the use of expensive acrylamide monomer and Bis co-polymer, or agarose or starch, and generally to improve the performance of electrophoresis apparatus.

The electrophoresis apparatus in accordance with the invention achieves these objects by providing a slab gel which is subdivided into a plurality of "micro" slab gels by means of for example thin plastic sheets, the term "micro" herein referring only to the small thickness of the individual micro gels comprising the slab gel, and not to their other dimensions, the so subdivided slab gel hereinafter designated a multi-gel or multi-gel slab gel. After the run, the multi-gel may be readily peeled into the individual micro gels for further assaying or processing, e.g. staining by different staining solutions to separately identify and perhaps quantify enzyme, protein or other analytes that may not necessarily have been adequately resolved for identification and/or quantification with a single staining solution.

Thus as a basic unit there is provided a divider means for casting a multi-gel slab gel therein which comprises a plurality of spacer sheets with one or more thin divider sheets.

Also provided according to the invention is a multi-gel casting unit (of which at least three distinct types may be provided—see definitions below) adapted for use in the production of a multi-gel slab gel, whether of polyacrylamide, agarose, starch or any other suitable gel. Said multi-gel casting unit may be adapted for use as a disposable unit, or as a unit of which at least some parts may be used repetitively. The multi-gel casting unit may be provided with a multi-gel slab already cast therein. Or it may be provided ready for the casting therein of a multi-gel slab gel of the user's choice. The multi-gel casting unit may be adapted for use together with existing electrophoresis apparatus available in the trade; or it may be provided together with electrophoresis apparatus specially adapted for efficient use of the multi-gel casting unit and multi-gel slab gel in accordance with the invention.

The invention also provides an electrophoresis apparatus which makes use of the multi-gel slab gel in accordance with the invention by the vertical electrophoresis method.

Although vertical electrophoresis generally produces superior separations and sharpor bands than horizontal electrophoresis, and may play an important role in the testing and defining of new enzyme systems, the complexity of design of the apparatus and complicating factors such as the need for waterproofing and adequate cooling are often inhibitory as far as routine applications with known enzyme systems are concerned. Horizontal electrophoresis, on the other hand, because of the simplicity of apparatus design, and ease of manufacture and assembly, and hence relative cheapness, offers an attractive alternative, particularly for routine electrophoresis analysis, even although the quality of separations and the sharpness of the bands achieved may in general be somewhat inferior to those typically obtained with the vertical version.

A further object of the present invention is therefore to adapt the multi-gel casting unit for casting a gel therein to render it suitable for use in a horizontal electrophoresis apparatus.

Yet a further object of the invention is to provide a horizontal electrophoresis apparatus which permits an economy in the use of expensive acrylamide monomer and Bis co-polymer, or alternatively agarose or starch, and generally to improve the ease of operation and performance of a horizontal electrophoresis apparatus. (In the descriptions below the term "non-conducting" used in describing or categorising materials invariable refers to the electrical rather than to the heat conducting properties of the material, unless otherwise indicated.)

DETAILED DESCRIPTION OF THE INVENTION

In accordance with a first stage of the invention there is provided a multi-gel slab for use in gel electrophoresis comprising a gel which is subdivided into two or more thinner gels separated by means of divider sheets, for example thin plastic divided sheets, for example plastic sheets of from 6 to 250 $\mu m$ in thickness, preferably about 50 $\mu m$ in thickness. The gel may be a polyacrylamide gel, an agarose gel, a starch gel or a gel of any other material suitable for use in gel electrophoresis.

In accordance with a second aspect of the invention there is provided a divider means comprising a plurality of spacer sheets provided in the form of two stacks, each spacer sheet in one stack being preferably of substantially equal thickness to that of the corresponding spacer sheet in the other stack, and with thin divider sheets affixed between each pair of successive spacer sheets in one stack and the corresponding pair of spacer sheets in the other stack. The divider sheets may comprise polyethylene, polyester or any other suitable thin plastic sheeting material, including heat-shrink sheeting material, with the proviso that if the slab gel is to be of such importance that the divider sheets are secured to the spacer sheets, and the bottom spacer sheets are secured to a base plate, it is preferred that the attachments be made with double-sided adhesive tape, or by gluing or by suitable heat treatment or by means of ultrasonic energy.

Another embodiment of the divider means is one in which the set of divider sheets are split in two or more sets by suitably punching out the gap or gaps.

Still another embodiment of the divider means is one in which one or more rows of holes are punched into the set of divider sheets.

Still another embodiment of the divider means is one in which the spacer sheets are all of substantially equal thickness.

In still another embodiment of the divider means as claimed, in which the spacer sheets are of variable thickness, it is provided that any spacer sheet in one stack be substantially of the same thickness as the corresponding spacer sheet in the other stack.

It is further contemplated that novel slab gel of this invention can be preferably as the essential element of more comprehensive embodiments—for example to various embodiments of a sub unit of, or for use in, an electrophoresis apparatus (vertical or horizontal) in accordance with the invention. These embodiments may include the following:

(i) A multi-gel cartridge assembly unit, which comprises a sub base plate, optionally a set of spacer stops, if appropriate fixedly secured to the sub base plate, and optionally a divider means. The multi-gel cartridge assembly unit may optionally be provided as a disposable unit, preferably with a matching top plate (the latter in one part or in two, three or four parts); or it may be provided, optionally partly or wholly in knockdown form, as part of a "kit" for use in a vertical and/or horizontal electrophoresis apparatus. (It is to be noted that we distinguish between a multi-gel cartridge assembly unit, which is used in a (split) multi-gel cartridge unit, and an in situ multi-gel casting assembly unit, a term later defined, which is used to describe a multi-gel casting unit built up in situ in a horizontal electrophoresis apparatus with fixed buffer chambers.)

(ii) A multi-gel cartridge unit, for use in the first instance in a vertical electrophoresis apparatus, and which represents an elaboration on a multi-gel cartridge assembly unit (i), which may be used as a starting unit for the construction of said cartridge unit. It comprises a multi-gel cartridge assembly unit (i), together with a one-piece top plate fixed in position by means of side stops, for example by means of waterproof adhesive tape and provision for waterproofing of the cartridge unit.

It is nevertheless possible to use the multi-gel cartridge unit also in a horizontal electrophoresis apparatus, for example by adding further gel-forming mixture to the top of the cartridge unit after the samples had been dispensed into the sample wells, and allowing the additional gel-forming mixture to set.

(iii) A "split" multi-gel cartridge unit, for use in the first instance in a horizontal electrophoresis apparatus, which may also be constructed using a multi-gel cartridge assembly unit (i) as starting unit. It differs from the cartridge unit (ii) in that the top plate is provided in more than one, preferably two (but optionally three or even four), parts which in assembly are placed side by side such as to provide a gap or slot of a few millimeters between each pair of such parts. By judicious choice of the relative size of the parts of the top plate, the gap or slot (in the case where the top plate is provided in two parts) may be produced towards one end of the split multi-gel cartridge unit, or approximately along a central dividing line of said cartridge unit, or anywhere in between. As will become apparent in the description below, the slot is provided to enable a set of sample wells to be formed in the multi-gel slab gel by means of a sample comb when a multi-gel slab gel is cast in the split multi-gel cartridge unit.

It is to be noted further; ($\alpha$) that the split multi-gel cartridge unit may for example be adapted for more effective use in preparative gel electrophoresis, by providing the top plate in three or four parts, thus to produce two or three sets of sample wells; ($\beta$) that the sets of divider sheets provided in the split multi-gel cartridge unit must, of course, also be provided with one or more slots, to match with the slots(s) in the top plate; and ($\gamma$) that while the split multi-gel cartridge unit is provided in the first instance of use in a horizontal electrophoresis apparatus, it may be adapted for use also in a vertical electrophoresis apparatus, for example by filling up the sample wells, after the samples have been dispensed therein, with additional gel-forming mixture, allowing this mixture to set, and covering over the slot or slots, for example with waterproof adhesive tape.

It may also be noted that in all the embodiments described above (i.e. (i) to (iii)) the size of the divider means (and hence the multi-gel slab gel to be provided therein) that may be accommodated may be varied by varying the positions of the spacer stops provided for example on the sub base plate.

Thus in accordance with one embodiment of the third aspect of the invention there is provided a multi-gel cartridge assembly unit for use in constructing a multi-gel casting unit for use in an electrophoresis apparatus comprising (a) a sub base plate comprising a sheet of a suitable non-conducting material, preferably glass;
(b) optionally a set of spacer stops affixed to said sub base plate, for example by gluing;
(c) a divider means in accordance with the second aspect of the invention;
(d) optionally a top plate comprising a sheet of a suitable non-conducting material, preferably glass, said top plate being provided either as a single part or in two, three or four parts, the top plate being of substantially the same length and width as the sub base plate, with the proviso that should the top plate be provided in more than one part, the size(s) of the gap(s) or slot(s) to be provided in assembly between the parts is/are to be considered as part of said dimensions of the top plate.

In accordance with a second embodiment of this aspect of the invention there is provided a multi-gel cartridge unit for casting a multi-gel slab gel therein comprising (e) two sheets (i.e. a sub base plate and a top plate) of a suitable non-conducting material, preferably glass, of substantially the same width and length; connected by
(f) two substantially rod-shaped side stops adapted to separate the two sheets (e) along two opposite sides and substantially to seal off these ends, preferably at least one of said side stops being provided with a cylindrical space with a fitted plunger rod, the side stops comprising a non-conducting material;
(g) a set of spacer stops, provided inside the cartridge unit and affixed to one or both of said sheets (e), for example by gluing,
(h) a divider means in accordance with the second aspect of the invention;
the thin divider sheets being stretched taut during or after assembly by placing the stacks of spacer sheets in position behind the appropriate spacer stops and/or heat shrinking the thin divider sheets if made of a heat-shrink material.

In accordance with a third embodiment of the third aspect of the invention there is provided a split multi-gel cartridge unit for use in an electrophoresis apparatus comprising (i) a sub base plate comprising a sheet of a suitable non-conducting material, preferably glass;
(j) a set of spacer stops affixed to said sub base plate, for example by gluing;
(k) a divider means in accordance with the second aspect of the invention;
(l) a top plate comprising a sheet, provided in two, three or four parts, of a suitable non-conducting material, preferably glass, the parts of the top plate together with gap(s) or slot(s) of about 5 mm width provided between adjacent parts in assembly having substantially the same dimensions (other than thickness) as the sub base plate under (i): and
(m) optionally two side stops comprising for example rods;

there being provided gap(s) or slot(s) in the set of thin divider sheets of the container means (k) to match the gap(s) or slot(s) provided in the top plate in assembly; and the thin divider sheets being stretched taut during or after assembly by placing the stacks of spacer sheets in position behind the appropriate spacer stops and/or heat shrinking the thin divider sheets if made of a heat-shrink material.

If the top plate comprises only two parts, the relative sizes of the two parts may be selected such that the gap or slot is provided close to (e.g. at a distance of about 10 to 20 mm from) one of the open ends of the split multi-gel cartridge unit, or approximately along a central dividing line of said cartridge unit, or at any desired position in between.

In the embodiments described above the side stops (f) or (m) may have a substantially circular, square, hexagonal or any other suitable cross section.

The side stops (f) or (m) may be suitably moulded plastic tubes or glass tubes and/or rods, optionally provided with indentations on the first and second or third and fourth quadrants in their cross-section, to accommodate the edges of the glass sheets.

Alternatively the side stops may comprise, on both but at least on one side, a first tube, for example a glass tube, with fitted plunger rod, and optionally on the other side a rod, for example a glass rod, both tubes or tube and rod being provided with larger half-tubes, the inner diameter of which is such that the first tube or rod fits snugly therein. These half tubes may for example comprise glass or plastic tubes longitudinally cut in half.

The side stops may be affixed in position to the two sheets of non-conducting material (e) or (i) and (l) by gluing or by means of adhesive tape.

The spacer stops (b), (g) or (j) in all three embodiments may conveniently be wedge shaped and are preferably constructed of a non-conducting material such as glass or a plastic material, for example polymethylmethacrylate. Other embodiments of the spacer stops, if indeed provided, are also possible (see below).

In practice it is convenient to standardise on a (split) multi-gel cartridge unit of a fixed total thickness, for example 12 mm, of which the multi-gel slab gel occupies a thickness of for example about 8 mm. Occasions may arise where a desired analyte in a sample (or set of samples) may be present in such low concentration (in the case of an enzyme) has such a low activity that it becomes desirable to minimise the number and/or thicknesses of the micro gels comprising the multi-gel slab gel, for example by reducing the multi-gel slab to a single micro gel. In such a case the thickness of the sub base plate and/or of the top plate may be increased commensurably as the number and/or thickness of micro gels used in the multi-gel cartridge unit is reduced. For example, a single microgel of about 2 mm thickness (or two of about 1 mm each) may be produced by increasing the thickness of the sub base plate and of the top plate to 6 and 4 mm, respectively. (For this type of adaptation, the side stops and sample comb(s) will have to be adapted.)

As disclosed in the priority application, 88/2019, filed Mar. 22, 1988, in the Republic of South Africa, the contents of which form part of this disclosure, the invention permits individual gel layers to be as thin as 0.1 mm, so that in light of the preceding paragraph, individual layers may range in thickness from about 0.1 to about 8 mm.

In accordance with a fourth aspect of the invention there is provided a multi-gel casting unit in accordance with any one of the embodiments of the third aspect of the invention together with a pre-packed multi-gel slab gel in accordance with the first aspect of the invention provided therein.

In accordance with a fifth aspect of the invention there is provided a vertical electrophoresis apparatus adapted for use with, and in combination with, a multi-gel cartridge unit with or without a packed multi-gel slab gel provided therein in accordance with, respectively, the second embodiment of the third aspect and the first aspect of the invention, comprising (a) a lid member, adapted to enclose a top buffer chamber, and provided with an electrode connected to an electrical connection point on the exterior of said lid member, the electrode being adapted to be immersed in the buffer solution of said top buffer chamber when the lid member is placed in position;

(b) a top buffer chamber member adapted to closely fit into the top section of a cooling chamber member and provided with a slot in its bottom wall into which the multi-gel cartridge unit, optionally provided with a multi-gel slab gel cast therein, in accordance with, respectively, the second embodiment of the third aspect and the first aspect of the invention, is to be fitted;

(c) a cooling chamber member, suitably provided with inlet and outlet openings for circulating for example tap water, the base wall of said cooling chamber member being provided with a slot into which the multi-gel cartridge unit, optionally provided with a multi-gel cast therein, as defined under (b), is to be fitted, said base wall of the cooling chamber being adapted to provide the top aspect of a bottom buffer chamber member and to ensure a close fit when the apparatus is assembled;

(d) a bottom buffer chamber member provided with an electrode connected to an exterior electrical connection point and spacers on the inside walls of said bottom buffer chamber member adapted to ensure that excess electrode buffer can pass between the outside wall of the cooling chamber member and the inside wall of said bottom buffer chamber member in assembly, to ensure adequate electrical contact between the buffer solution and the multi-gel cartridge unit with or without associated multi-gel slab gel, as well as optionally spacers provided in the back and front aspects of said bottom buffer chamber member to ensure a close fit when the apparatus is assembled; and (e) a pair of flexible seals for providing a watertight seal for a multi-gel cartridge unit, optionally with associated multi-gel slab gel provided therein, as defined under (b), when fitted into the slots provided in the top buffer chamber (b) and cooling chamber member (c).

The electrodes preferably comprise platinum wire electrodes fitted preferably horizontally on the surface of a cross-member provided in the lid member and in the bottom wall of the bottom buffer chamber member.

Each of the interfitting units (a), (b), (c), and (d), apart from the electrodes and external electrical connecting points, is constructed entirely or substantially entirely of a suitable non-metallic, non-conducting material, preferably a cast or moulded thermoplastic or thermosetting plastics material. Alternatively the units may be constructed from polymethylmethacrylate sheeting or any other suitable plastics sheeting material, secured together for example by gluing.

The flexible seals may be constructed of any suitable rubber-like material, for example Dow Corning ® Q3-3321 RTV High Strength Silicone Mouldmaking Rubber, which is a fluid that sets into a solid rubber component after mixing with a catalyst. Optionally the seals may be provided fixedly in the slots in the members (b) and (c).

Preferably the slots provided in the appropriate walls of the top buffer chamber member and cooling chamber member are wedge-shaped, the walls of each slot being at an angle of about 15° to 20° relative to the vertical, such that the slots are narrower at their outside ends than at their inside ends. When the multi-gel cartridge unit has been placed in position together with the pair of flexible seals, pressing the top buffer chamber member (b) downwards may then be used to ensure watertight seals between the multi-gel cartridge unit and the slots at both ends of the cartridge.

In the assembled vertical electrophoresis unit, provision may optionally be made for the continuous or intermittent mixing of the buffer solution in the two buffer chambers, e.g. by providing means for pumping buffer solution from the bottom buffer chamber member into the top buffer chamber member. It will be appreciated by those skilled in the art that provision may be made for the use of a second buffer chamber, in an "in tandem" arrangement, both with the top buffer chamber member and with the bottom buffer chamber member.

In accordance with a sixth aspect of the invention there is provided a casting stand adapted for use in casting a multi-gel slab gel in accordance with a first aspect of the invention into a multi-gel cartridge unit in accordance with the second embodiment of the third aspect of the invention, in combination with a vertical electrophoresis apparatus in accordance with the fifth aspect of the invention, the casting stand comprising (a) a stand capable of supporting the assembled parts (b) and (c) of the vertical electrophoresis apparatus in accordance with the fifth aspect of the invention, there being provided a hole, preferably tapered, substantially in the centre of the top surface of the stand into which a funnel may be suspended;

(b) a funnel provided with a flexible rubber band or ring (e.g. constructed of Dow Corning ® silicone rubber) along its rim, to ensure a watertight seal with (c) a connecting piece comprising a combination of a casting stand sub base plate provided with a slot, of length shorter or about equal to the diameter of the funnel at its rim, and a flexible rubber seal, for providing a watertight seal between said sub base plate and the base of the cooling chamber member of the electrophoresis apparatus in accordance with the fifth aspect of the invention, the seal being provided with a slot which encloses the bottom end of the multi-gel cartridge unit when the latter is placed in position in the parts (b) and (c) of the vertical electrophoresis apparatus;

(d) one or two, preferably two, reservoirs, supported on a stand, and connected by tubing via a tap, preferably a three-way tap if two reservoirs are provided, and by means of flexible tubing to the bottom end of the funnel; and (e) a sample comb comprising a plate provided with a serrated edge or a set of teeth at one end or two opposite ends, suitably adapted to enable the production of a plurality of sample wells in the top of the multi-gel slab gel while the gel-forming mixture is polymerising.

The object of the casting stand in accordance of this aspect of the invention is to provide a means for casting a multi-gel slab gel in accordance with the first aspect of the invention in the multi-gel cartridge unit in accordance with the second embodiment of the third aspect of the invention while said multi-gel cartridge unit and sample comb are positioned in place within the parts (b) and (c) of the vertical electrophoresis apparatus in accordance with the fifth aspect of the invention. For this purpose the assembled electrophoresis apparatus, with the lid member and bottom buffer chamber removed, and with the multi-gel cartridge unit and sample comb placed in position, is placed on top of the stand as described, such that the funnel, provided with a sealing band or ring along its rim and used together with the connecting piece, makes a watertight connection with the base wall of the cooling unit.

The required amount of solution containing the ingredients for gel formation may now be fed by gravity from one reservoir via the three-way tap and the tubing into the funnel, followed by the upward displacement at a controlled rate into the multi-gel cartridge unit of said solution by another, more dense liquid, for example a 30% sucrose solution. It is important, particularly if the partitioned micro chambers are very narrow, that the liquid to be polymerised should flow slowly upwards in between the plastic divider sheets of the multi-gel cartridge unit, to prevent the formation and retention of air bubbles in the micro chambers. It is possible to use only one reservoir and to feed the liquid containing the ingredients for gel formation and the displacement solution to the bottom of the funnel successively from the same reservoir.

The casting stand may be used to case multi-gel slab gels successively in several multi-gel cartridge units, and these cartridge units with prepacked gel may then be removed and stored for later use. Instead of using part of the assembled vertical electrophoresis apparatus for supporting the multi-gel cartridge unit and sample comb, a suitable second stand may be used, in the top surface of which is provided a slot to accommodate a multi-gel cartridge unit with associated flexible seal and the sample comb. It is also possible to adapt the casting stand, when making use of such a second stand, to provide for the simultaneous or successive casting of multi-gel slab gels in several multi-gel cartridge units in one operation.

Many variations of the casting stand in accordance with this aspect of the invention described above may be used by those skilled in the art, and these embodiments also fall within the scope of the invention when use is made of in situ casting of a multi-gel slab gel in a multi-gel cartridge unit in accordance with the first aspect and second embodiment of the third aspect of the invention by upward flow of the gel-producing solution into the multi-gel cartridge unit.

For example, a person skilled in the art would readily be able to adapt a multi-gel cartridge unit in accordance with the invention and the method of casting a gel therein for use in stacking and gradient gel electrophoresis.

It is possible also to cast a multi-gel slab gel in a multi-gel cartridge unit without the use of a sample comb, thus to produce a smooth top surface for the multi-gel slab gel. This permits placing of for example a tube gel in which a sample has already been subjected to an electrophoresis run on the top of the multi-gel slab gel and then to carry out a second electrophoresis run, thus to effect two-dimensional electrophoresis.

In the simplest version of a horizontal electrophoresis apparatus in accordance with the invention the apparatus comprises two buffer chambers (with the electrodes preferably contained in removable lids) mounted on an extended glass base plate, such as to provide a space between said buffer chambers into which a multi-gel casting unit in accordance with the third aspect of the invention (for which we use the term in situ multi-gel casting assembly unit) together with a multi-gel slab gel provided therein may be constructed, the apparatus being adapted to provide direct electrical contact between the multi-gel slab gel and the two buffer chambers, cooling being provided for example by means of a lower and optionally an upper metal plate, each optionally provided with a cooling coil through which cooling water may be circulated.

As will be seen below, many different embodiments of this aspect of the invention are possible, particularly when the buffer chambers are removably affixed to the extended base plate. In the preferred embodiments, the use of wicks typical of horizontal electrophoresis in current use is dispensed with. An electrophoresis apparatus operating without the use of wicks has the following advantages:

(i) Optimal electrical contact may always be ensured;
(ii) The need for high-capacity electrical power units is reduced, since in state-of-art apparatus using wicks, the greater part of the electrical resistance in the circuit is due to the wicks;
(iii) In the absence of wicks (i.e. with direct electrical contact between the slab gel and the buffers) higher applied voltages may be used, leading to reduced running times; with wicks, increasing voltages may result in undue heat generation in the wicks (the "weak links" in the circuit), leading to increased evaporation of liquid and possibly drying of the wicks and the risk of a fire if a run is left unattended, for example overnight.

If preferred, however, wicks may still be used, as described below for one of the embodiments. Thus, in accordance with a seventh aspect of the invention, there is provided a horizontal electrophoresis apparatus adapted for use with, and in combination with, a multi-gel casting unit, optionally with associated multi-gel slab gel provided therein in accordance with the fourth aspect of the invention, the horizontal electrophoresis apparatus comprising (a) an extended base plate comprising a sheet of a substantially smooth, non-conducting material, preferably glass;
(b) two buffer chambers, which may be identical and/or of substantially equal dimensions, each for example comprising four walls defining a chamber, which may for example be rectangular or square, the wall construction being affixed, optionally removably, to the extended base plate, with the inner, facing walls of the two chambers each provided with an opening or slot, the buffer chambers optionally provided with electrodes;

(c) a multi-gel casting unit in accordance with the third aspect of the invention positioned between the buffer chambers;

(d) a sample comb;

(e) a bottom cooling means, and optionally a top cooling means; and (f) optionally, if electrodes are not provided in the buffer chambers, a loose-fitting lid for each buffer chamber on to the bottom surface of which may be affixed an electrode, adapted such that the electrode is submerged in buffer solution when the lid is placed in position, the electrode being preferably connected electrically to an electrical contact point provided on the exterior of the lid, placed for example on the top surface of the lid.

The buffer chambers (b), which may be constructed of polymethyacrylate or any other suitable non-conducting material, for example strips of polymethylmethacrylate sheeting glued together, or which may comprise a moulded plastics wall construction, are affixed, either fixedly or removably, on to the extended base plate such as to define a space between said buffer chambers into which the multi-gel casting unit of desired size (particularly length) may be provided.

The multi-gel casting unit may be a multi-gel cartridge unit or a split multi gel cartridge unit, as for the second or third embodiment of the third aspect of the invention, with or without a multi-gel slab gel according to the first aspect of the invention provided therein prior to assembly of the apparatus.

Since the buffer chambers may be constructed relatively cheaply, the assembly comprising the extended base plate, optionally constructed of a suitable plastic material (for example integrally with the fixed buffer chambers), the fixed buffer chambers and multi-gel casting unit (optionally in knockdown form) may be provided as a disposable or partially disposable unit.

Alternatively, the spacer stops may be provided integrally with the plastics extended base plate, and a container means and reusable top plate (in one or more parts) provided for insertion and fixing in position by the user by means of adhesive tape.

As a further alternative the multi-gel casting unit may be built up in situ by the user from spacer sheets and divider sheets separately provided, the latter for example in the form of a roll of a plastic film, or from an in situ multi-gel cartridge assembly unit separately provided.

Instead of being provided on the extended base plate in the form of integrally moulded or affixed spacer stops, for example as four wedge-shaped stops, the spacer stops may comprise four strips of plastic sheet, for example of polymethylmethacrylate, provided in the inner walls of the buffer chambers. Alternatively, the four spacer stops may comprise recesses provided in the inner corners of the buffer chamber walls.

As a further alternative the buffer chambers may be adapted to be slidingly affixed to the extended base plate, preferably of glass, for example with the use of a viscous lubricant, optionally but preferably with the outside walls of the buffer chambers extending around the extended base plate to provide guiding grooves in which the buffer chambers may slide, the slots provided in the inner walls of the buffer chambers being preferably adapted by suitable contouring such that the slots together with the contiguous surface of the extended base plate being adapted to be capable of receiving in a watertight fit the ends of a (split) multi-gel cartridge unit, for example by providing a rubber lining therein.

In yet another alternative the extended base plate may be dispensed with. In this, a preferred embodiment of the invention, the buffer chambers are each provided with its own bottom wall, for example of a plastics material for example provided integrally with the other walls, there being provided in the inside wall of each buffer chamber, for example about half-way between the top and bottom of said inside wall, a contoured, tapered slot which, together with a flexible seal (as described for the component (e) of the vertical electrophoresis apparatus in accordance with the invention), is adapted to receive in a watertight fit an end of a (split) multi-gel cartridge unit. The (split) multi-gel cartridge unit may rest on the top surface of a bottom cooling means.

The sample comb for use in a horizontal electrophoresis unit in accordance with the invention may comprise a length of a moderately thick sheet, of thickness, for example, about 10 mm, of, for example, polymethylmethacrylate, with affixed at right angles thereto a row of teeth or a serrated strip adapted to produce in use a plurality of sample wells in a multi-gel slab gel cast in a multigel casting unit when the gel mixture has set after casting. Preferably the protruding length of the teeth in such that the teeth span the full depth of the multi-gel casting unit. If the top plate comprises more than two parts, the sample comb must be provided appropriately with more than one row of sample teeth or serrated strips; or more than one comb may be used alongside each other.

Alternatively, individual teeth may be fitted slidingly and removably into slots, preferably rubber-linked, in the sheet, in such a way that each tooth may be manipulated separately. The teeth may thus be adjusted for any thickness of multi-gel casting unit, and some of the teeth may be withdrawn as desired. This facility adds further flexibility to the horizontal electrophoresis system, in that, should the full complement of samples normally used in an electrophoresis run not be available, a narrower multi-gel casting unit may be constructed, the appropriate teeth from the sample comb removed, and the unoccupied space(s) of the multi-gel casting unit filed with one or two suitably sized blocks. In this way, savings may be effected in the ingredients used by constructing a smaller multi-gel casting unit and thus a small multi-gel slab gel, and an electrophoresis run carried out with a reduced number of samples.

The advantage of being able to provide sample wells in a position in the multi-gel slab gel other than close to its one end, for example approximately along a central dividing line, will become apparent from the following considerations. In the art, analytes in samples are usually separated electrophoretically by utilising the movement of anionic species (i.e. species carrying a net negative charge) in the electric field. The analytes usually contain both weakly acidic and weakly basic groups, and the net charges on these species depend on the pH employed in the system. The selected pH is therefore largely determined by the nature of for example the enzyme or protein system being analysed for, but the nature of the sample (for example whether it is from plant or animal tissue) may have an important influence on the choice of pH. For optimum separation of the analytes, the optimum pH and buffer composition for the system must therefore be evaluated experimentally.

Thus, if the pH is too low, some of the analytes may bear a net positive charge, and these cations would then migrate in the "wrong" direction during electrophoresis, disappearing into the cathode buffer solution. They would therefore not be detected when the zymogram is subsequently developed.

Electrophoresis with samples places in sample wells formed for example approximately along a central dividing line of the multi-gel slab gel may therefore produce zymograms with both a cationic and an anionic component in which the analytes may have been resolved. This facility is especially useful for optimising experimental conditions (e.g. buffer pH) for full, final electrophoresis runs with new enzyme/protein systems and/or known enzyme/protein systems with new types of sample.

The bottom cooling means may comprise a moderately thick solid metal plate, of thickness for example from 1 to 10 mm, optionally but preferably provided with a metal tube (preferably formed into coils) affixed thereto through which for example cooled water may be circulated for carrying away the heat generated in the apparatus during an electrophoresis run. The optional top cooling means may similarly comprise a moderately thick solid metal plate, of thickness for example from 1 to 10 mm, optionally provided with a metal tube (optionally coiled) affixed thereto through which for example cooling water may be circulated.

Alternatively, one or both of the cooling means may comprise a shallow cooling chamber provided with an inlet and outlet connection for fitting hoses of for example rubber or PVC tubing thereto for the circulation of for example cooling water. The chambers may each be constructed of a moulded plastic material or of polymethylmethacrylate sheeting, except for the wall making contact with the base plate or top plate of the multi-gel casting unit, which is preferably constructed of a better heat conducting material such as glass. As mentioned above, if of adequate size, a bottom cooling chamber constructed in this way may be used to replace the base plate (a) above, i.e. the multi-gel casting unit and optionally also the buffer chambers may be directly provided on or mounted on to the top wall of the shallow cooling chamber.

The electrodes, which typically comprise metal, for example platinum, wires, may be appropriately mounted in the buffer chambers. Alternatively, the electrodes may comprise metal wires fitted on to bottom members provided in optional loose-fitting cover plates (i.e. lids), constructed of a non-conducting material, for the buffer chambers. As a further alternative, particularly in an embodiment of the invention in which part (including the buffer chambers) or the whole of the horizontal electrophoresis apparatus is to be disposable, the electrodes may comprise conductive carbon rods, preferably provided in the buffer chambers. In all these embodiments provision is made for external electrical connection points for connecting the electrodes to the high-voltage d.c. power supply.

In practice, the horizontal electrophoresis apparatus in its simplest version, optionally with fixed chambers, may be assembled and operated as follows. The two buffer chambers are affixed to the extended base plate (if not provided in integrally fixed form), for example with silicone glue, ensuring the desired distance between the inner walls of the buffer chambers. If not provided in the inner walls of the buffer chambers (whether as protruding members or as recess), the spacer stops may be affixed into position on the base plate close to the corners of the square or rectangular area defined by the inside walls of the buffer chambers. A spacer sheet is affixed into position on each side by means of double-sided adhesive tape, and a divider sheet is stretched taut across the spacer sheets and affixed thereto by means of the exposed top layer of the double-sided adhesive tape. Another spacer sheet is similarly affixed on each side and a divider sheet stretched across and affixed to the spacer sheets as described. In this way a stack of spacer sheets is built up along both sides of the base plate, with divider sheets stretched therebetween, until each stack reaches the top level of the spacer stops. The loose ends of the divider sheets may now be trimmed off. The space into which the gel is to be cast has now been subdivided by means of the divider sheets into a plurality of narrow chambers, still open at both ends. (Heat-shrinking of the divider sheets, to produce tautness, may now be performed, if required.)

The top glass plate of the multi-gel casting unit is now placed in position, and the appropriate sample comb placed on top, with its teeth projecting downwards through the slot into the multi-gel casting unit, and temporarily fixed in position by means of adhesive tape stretched across the top surface of the sample comb sheet and around the spacer sheet stacks, and preferably around part of the bottom surface of the base plate.

The slot in the inside wall of one of the buffer chambers is now temporarily sealed off. This may be achieved for example by means of a rubber plug, adhesive tape, etc. We have found it convenient to place a polymethylmethacrylate block, of the dimensions of the inside space of the appropriate buffer chamber, in the chamber, to substantially fill the chamber, and to cover over the outside sealingly with adhesive tape.

The entire assembly may now to be placed inside a transparent plastic bag, and the plastic bag tied tightly (for example) by means of string or by means of masking tape) around the assembly to substantially seal off the outside of the assembly, but leaving access to the other buffer chamber. (This operation is carried out in such a way that the operator can still see inside the multi-gel casting unit.) Preferably a plate (for example of either glass or polymethylmethacrylate) of dimensions similar to that of the assembly or at least the dimensions of the multi-gel casting unit, is placed on both sides on the outside of the plastic bag before the latter is tied down. This prevents sagging or bulging of the plastic bag when the gel mixture is poured. The gel-forming agent, for example a starch solution or an acrylamide solution, is now poured through the slot in the buffer chamber which has not been sealed off, while holding the apparatus in a vertical configuration, until the multi-gel casing unit space and the exposed parts of both slots are completely filled with the solution. Slight tilting of the apparatus helps in dislodging air bubbles. The apparatus is left in the vertical position until the gel has set, whereafter the plastic bag, the slot seal of the one buffer chamber and the sample comb are removed. The apparatus is now ready for use. It is to be noted that in this embodiment the gel itself provides a waterproof seal between the ends of the multi-gel casting unit and the inside walls of the buffer chambers.

With the apparatus placed in an horizontal position on to the bottom cooling means, the analysis samples may be dispensed into the sample wells, e.g. together with a dense sucrose solution and buffer solution according to known art. The appropriate buffer solutions are now added to the buffer chambers. The top cooling plate may then be placed on top of the multi-gel casting unit, the cover lids with the electrodes placed in position (if required), and electrophoresis started.

It will be appreciated by the person skilled in the art that many variations are possible in the details given above for assembling and using a horizontal electrophoresis in accordance with the invention, including assembly of a multi-gel casting unit and casting a multi-gel slab gel therein. For example, as mentioned earlier, by the judicious use of masking tape to tape down the plastic divider sheets bent around the edges of the base plate, it is possible to dispense with the use of spacer stops and double-sided adhesive tape.

After the electrophoresis run, the buffer solutions may be decanted or siphoned off, and the multi-gel slab dismantled by removing the top plate and cutting through the plastic layers along the insides of the spacer sheet stacks, e.g., by means of a scalpel, and the micro gels peeled off one by one for staining or further processing. It is also possible to remove only for example one of the micro gels, for staining, and to restart the electrophoresis run. This facility is particularly useful when testing new enzyme or protein systems for optimising electrophoresis conditions.

In the embodiment of the invention and the use of the apparatus described above, the multi-gel casting unit in which the multi-gel is to be cast is constructed directly on to the extended base plate of the horizontal electrophoresis apparatus with fixed buffer chambers. To permit the production of multi-gel casting units of variable size the electrophoresis apparatus in accordance with this aspect of the invention may be adpated as follows.

In this embodiment a multi-gel cartridge assembly unit according to the first embodiment of the third aspect of the invention is slided into position from the side (particularly if the buffer chambers are provided fixedly), the buffer chambers being provided on the bottom of their inner walls (and optionally also along part of the length of the side walls) with matching indentations, to substantially exactly accommodate the extremeties of the sub base plate when being slidingly placed into position. Optionally, instead of providing indentations in the inner walls and part of the side walls, the buffer chambers may also be provided with a sub base plate such that when the multi-gel cartridge assembly unit has been placed in position on the extended base plate, the sub base plates of the multi-gel cartridge assembly unit and those of the buffer chambers form a uniform sub base plate over substantially the entire length of the extended base plate. Silicone grease or vaseline may be used to ensure a watertight seal between the various parts of the apparatus.

We have found that when a multi-gel slab gel comprising starch is used with the horizontal electrophoresis apparatus without the use of wicks, the starch gel tends to lift and separate from the base plate causing leakage between the buffer chambers and short circuiting during an electrophoresis run, apparently owing to the phenomenon of endo-osmosis. This problem, at least as far as the leaking and short circuiting is concerned, may be readily overcome by using wicks to make electrical contact between the gel and the buffer chambers, or by the casting of narrow (e.g. 20 mm wide) strips of polyacrylamide gel on either side of the starch gel, to serve as "bridges" between the starch gel and the buffer solutions. For, in the embodiment making use of wicks, the multi-gel casting unit together with multi-gel slab gel cast therein may be suspended from the inside edges of the buffer chambers, with the wicks connecting the ends of the gel with the buffer solution. Under these conditions the buffer solutions cannot penetrate the multi-gel casting unit where the gel has become loosened from the sheets defining the casting unit.

To overcome possible complications owing to undesirably rapid changes occurring in the buffer solutions in the course of an electrophoresis run, use may be made of a pair of buffer chambers preferably on both sides of the multi-gel casting unit, for example affixed, preferably removably affixed, to the extended base plate in a tandem configuration, electrical contact between the buffer chambers on any one side being provided for example by means of a salt bridge or a wick, or by using buffer chambers each divided into two by means of a sintered glass partitioning wall.

DESCRIPTION OF THE DRAWINGS

The invention will now be described and its operation and application illustrated, by way of example, with reference to the following drawings, in which FIG. 1 shows a perspective view of a multi-gel casting unit (designated a multi-gel cartridge assembly unit) in accordance with one embodiment of the third aspect of the invention;

FIG. 2 shows a perspective view of another embodiment of a multi-gel casting unit (designated a multi-gel cartridge unit) in accordance with another embodiment of the third aspect of the invention;

FIG. 3 shows a plan view of the multi-stage cartridge unit shown in FIG. 2, showing further details of the construction;

FIG. 4 shows a perspective view of yet another embodiment of a multi-gel casting unit (designated a split multi-gel cartridge unit) in accordance with the invention;

FIG. 13 shows a side elevation of a casting stand in accordance with the sixth aspect of the invention, together with part of the vertical electrophoresis apparatus shown in FIG. 7;

FIG. 14 shows in perspective drawings parts of the casting stand shown in FIG. 13, to show greater detail of construction;

FIG. 15 shows a perspective drawing of a partially exploded view of part of a horizontal electrophoresis apparatus within fixedly secured buffer chambers in accordance with the seventh aspect of the invention;

FIG. 16 shows a plan view of the horizontal electrophoresis apparatus shown in FIG. 15, with a cast multi-gel slab gel with sample wells in position;

FIG. 17 shows a perspective drawing of one embodiment of a sample comb for use in producing sample wells in a multi-gel slab gel used in the horizontal electrophoresis apparatus shown in FIG. 15;

FIGS. 18a, 18b and 18c illustrate in plan views three embodiments of spacer stops that may be used in a horizontal electrophoresis apparatus in accordance with the invention;

FIG. 19 shows a perspective drawing of a metal cooling plate, to illustrate the use of a cooling coil for cooling the plate with for example tap water;

FIG. 20 shows a side elevation of one embodiment of an assembled horizontal electrophoresis apparatus in accordance with the invention;

FIG. 21 shows a comb with removable teeth for use in producing variable numbers of sample wells in a multi-gel slab gel of variable size for use in a horizontal electrophoresis apparatus;

FIG. 22 shows a plan view of a split multi-gel cartridge unit with sample wells produced approximately along a centre line of the cast multi-gel slab gel, the cover plate not being shown;

FIG. 23 shows a side elevation of part of a horizontal electrophoresis apparatus using pairs of buffer chambers in tandem;

FIG. 24 shows a side elevation of an exploded view of a horizontal electrophoresis apparatus in which the buffer chambers are slidingly and/or removably affixed to the extended base plate, with part of a multi-gel cartridge assembly unit;

FIG. 25 shows schematically a side elevation of an adaptation of a horizontal electrophoresis apparatus to an arrangement in which wicks are used;

FIG. 26 shows a perspective drawing of an embodiment of a buffer chamber in which a slot, contoured and lined with rubber to fit one end of a (split) multi-gel cartridge unit, is provided contiguously with the base plate (not shown), the end of a (split) multi-gel cartridge unit to be fitted sealingly into the slot by means of silicone grease.

FIG. 27 shows a preferred embodiment of a horizontal electrophoresis apparatus in accordance with the seventh aspect of the invention incorporating buffer chambers as illustrated in FIG. 26 and a cooling means; and FIG. 28 shows a perspective drawing of another embodiment of a buffer chamber with rounded slot in its inside wall, into which a (split) multi-gel cartridge unit in accordance with the third embodiment of the third aspect of the invention may be fitted via a flexible seal.

In FIG. 1, the numeral 2 generally represents a multi-gel cartridge assembly unit, in which 4 represents a glass sub base plate 6, 6', 6" and 6" are polymethylmethacrylate spacer stops glued in position to the sub base plate 4. 8 and 8' are spacer sheets provided in stacks (only one spacer sheet is shown here on each side) with thin plastic divider sheets 10 (only one example which is shown) affixed in between successive spacer sheets in each stack, and stretched taut between the two stacks.

Figure 5:
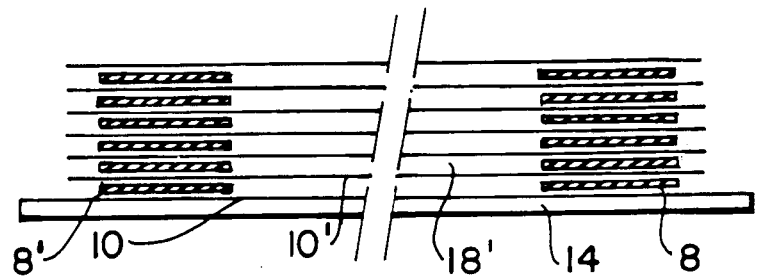
FIG. 5 shows schematically a side elevation of part of an assembly of plastic divider sheets interspaced with spacer sheets, to illustrate the division of a multi-gel casting unit compartment into micro compartments, here of equal thickness ("thickness" here referring to their smallest dimension)

In the multi-gel cartridge unit 12 in FIG. 2, two glass sheets 14 and 14', together with two side stops 16 and 16', enclose a chamber spacer 18. One side stop 16 comprises a glass rod 16.1, and an outer glass half-tube 16.2, while the other side stop 16' comprises a glass tube 16'.1, with a glass plunger rod 16'.3 fitted tightly but slidingly therein, as well as an outer glass half-tube 16'.2. The glass tube 16'.1 terminates short of the end of the outer half-tube 16'.2, leaving a gap 16'.4, the extension 16'.5 being a solid length of glass rod or, more conveniently, a piece of polymerized plastic "putty", on which the plunger rod 16.3 may rest. Thus if the glass plunger rod 16'.3 is withdrawn upwards during casting, air may escape via the gap 16'.4 up the tube 16'.1. The cartridge unit is held together by means of waterproof adhesive tape (not shown) stuck on the glass sheets and around the side stops.

FIG. 3 shows details in construction of the multi-gel cartridge unit shown in FIG. 2. The chamber space 18 is occupied by spacer stops 6 and 60' (and 6" and 6"', not shown) two stacks of spacer sheets 8 and 8', concealed behind the spacer stops 6 and 6', and tautly spanned between said spacer sheets, a multiplicity of thin divider sheets 10, 10' etc., to divide the chamber space 18 into a plurality of micro chambers 18'. The other numerals are as previously designated.

In FIG. 4, illustrating a split multi-gel cartridge unit, the top glass sheet is divided into two sections 14.1 and 14.2, leaving a gap 20 therebetween into which the teeth of a sample comb (as illustrated in FIG. 21) project during the casting of a multi-gel slab gel to leave sample wells when the gel has set, approximately along a centre dividing line of the cartridge. The plurality of thin divider sheets (not shown) is, of course, also provided in two sets such as to leave a gap coincident with gap 20 therebetween.

FIG. 5 show schematically in enlarged detail the construction of part of a multi-gel casting unit, the numerals having the meaning designated above, illustrating a plurality of spacer sheets (e.g. 8 and 8') and divider sheets (e.g. 10 and 10') enclosing micro compartments (e.g. 18') therebetween.

Figure 6C:
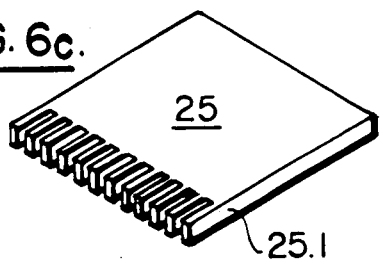
FIG. 6c shows a perspective drawing of a sample comb shown in FIG. 6b.
Figure 6B:
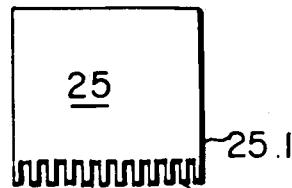
FIG. 6b shows a side elevation of a sample comb for use in the casting of a multi-gel slab gel in the casting unit.
Figure 6A:
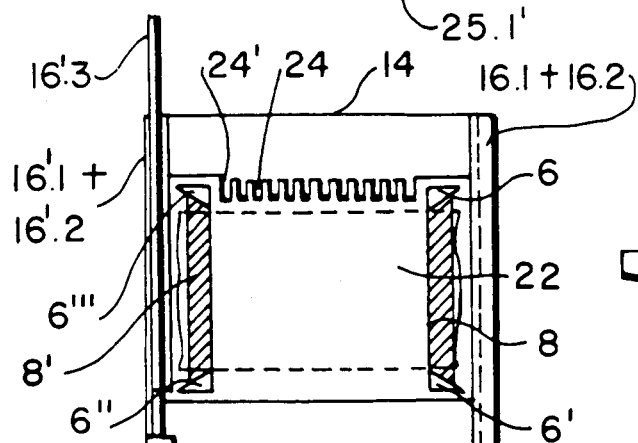
FIG. 6a shows a side elevation of the multi-gel casting unit of FIG. 2, with the multi-gel slab gel in accordance with the first aspect of the invention cast and ready for use.

In the illustration of an assembled multi-gel cartridge unit in FIG. 6a, the numerals are as defined before, the dotted area represents the multi-gel 22, with 24, 24', etc. indicating the plurality of sample wells in the top surface of the multi-gel slab gel left by the teeth 25.1, 25.1' etc. of the sample comb 25 (FIGS. 6b and 6c) after the comb 25 has been withdrawn, following setting of the gel-forming solution.

Figure 7:
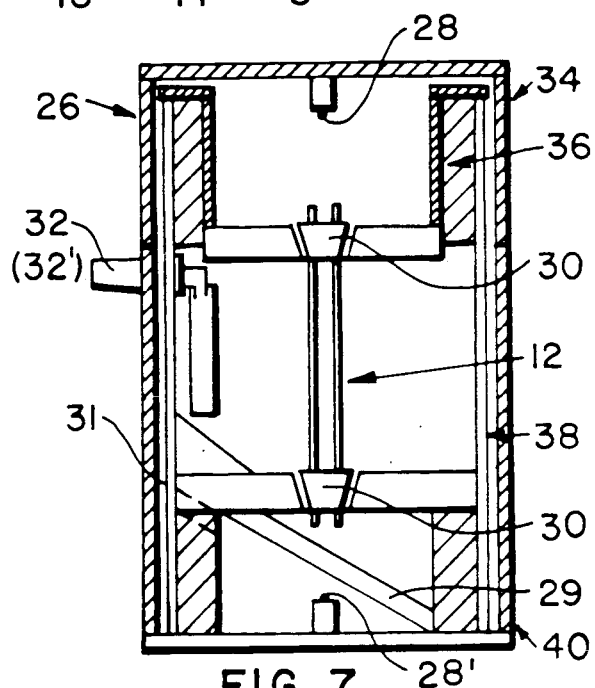
FIG. 7 shows a side elevation of an assembled vertical electrophoresis apparatus in accordance with the fifth aspect of the invention.

In FIG. 7 the numeral 26 generally indicates a vertical electrophoresis apparatus constructed largely of polymethylmethacrylate sheeting, with the multi-gel cartridge unit 12 (with cast multi-gel in position). The electrodes 28 and 28' are made of platinum wire. A deflector 29 is provided to deflect gas bubbles formed at the bottom electrode 28' up the space 31, to prevent them from becoming trapped in the bottom of the multi-gel cartridge unit 12 during an electrophoresis run. 30 and 30' represent rubber seals sealing off the multi-gel cartridge unit 12 in slots as indicated. 32 is the inlet port for cooling liquid, the outlet port 32' obscured by the inlet port not being shown. The successive members of the vertical electrophoresis apparatus, namely the lid member 34, the top buffer chamber member 36, the cooling chamber member 38 and the bottom buffer chamber member 40 are assembled together as shown.

Figure 8:
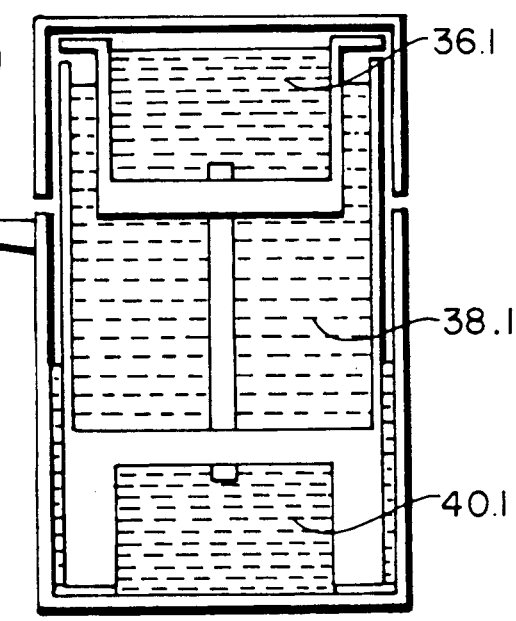
FIG. 8 shows schematically a side elevation of the vertical electrophoresis apparatus shown in FIG. 7, to indicate those parts occupied by buffer solutions and coolant.

FIG. 8 shows schematically the same vertical electrophoresis apparatus shown in FIG. 7, and is included to show the volumes occupied by the top buffer solution 36.1, the bottom buffer solution 40.1 and the coolant 38.1.

For the sake of clarity, details of construction of the individual members of the vertical electrophoresis apparatus are shown in FIGS. 9, 10, 11 and 12.

Figure 9:
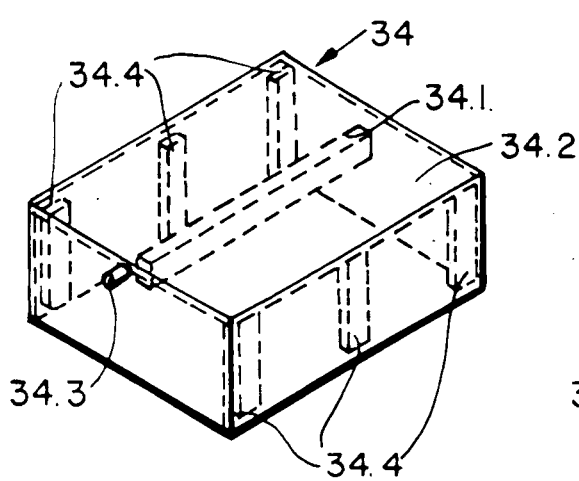
FIGS. 9, 10, 11 and 12 are isometric drawings showing details of the various members of the vertical electrophoresis apparatus in accordance with the fifth aspect of the invention shown in FIG. 7, which the figures represent, respectively, in chronological order, the lid member, the top buffer chamber member, the cooling chamber member and the bottom buffer chamber member.
Figure 10:
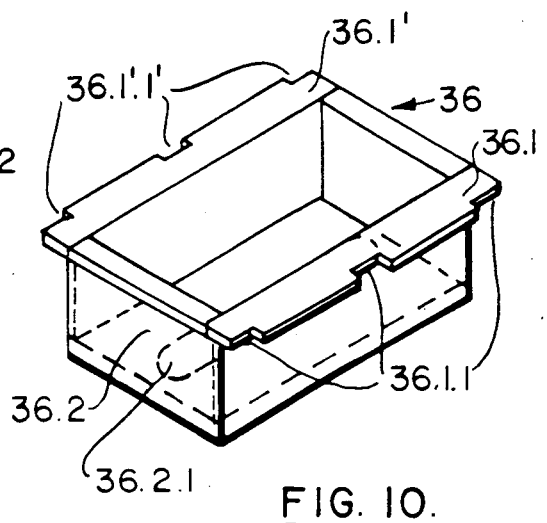

In FIG. 9, a cross member bar 34.1 is affixed to the roof sheet 34.2 of the lid member 34. To the bottom of the cross-member bar 34.1 is affixed a platinum wire (not shown) along its length, said wire being connected to an electrical connection point 34.3. The spacer strips 34.4 serve to assist in aligning the member during and in assembly.

The top buffer chamber member 36 (FIG. 10) in constructed as indicated, with flanges 36.1 and 36.1' provided with indentations 36.1.1 and 36.1'.1' to accommodate the spacer strips 34.4 (FIG. 9) in the assembled apparatus. The flanges 36.1 and 36.1' rest on the upper edges of the cooling chamber member 38. A tapered slot 36.2.1 is provided in its bottom member 3.2 into which the multi-gel cartridge unit (not shown) is to be fitted with the aid of a flexible seal (not shown).

Figure 11:
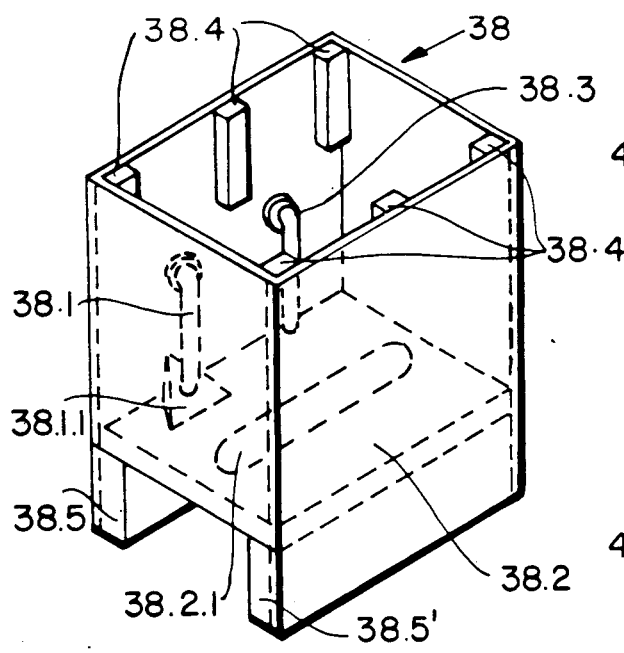

In FIG. 11, showing details of construction of the cooling chamber member 38, the bottom member 38.2 is also provided with a tapered slot 3.2.1, into which the multi-gel cartridge unit (not shown) is to be fitted by means of a flexible seal (not shown). 38.1 shows the interior part of the inlet tube 32 and 38.3 the interior part of the outlet tube 32' for cooling liquid, 38.1.1 being a means for deflecting the incoming cooling liquid upon entry through the inlet tube 38.1. Again, 38.4 are spacer strips serving to assist in aligning the top buffer chamber member 36 during and in assembly, as are the bottom positioning members 38.5 and 38.5'.

Figure 12:
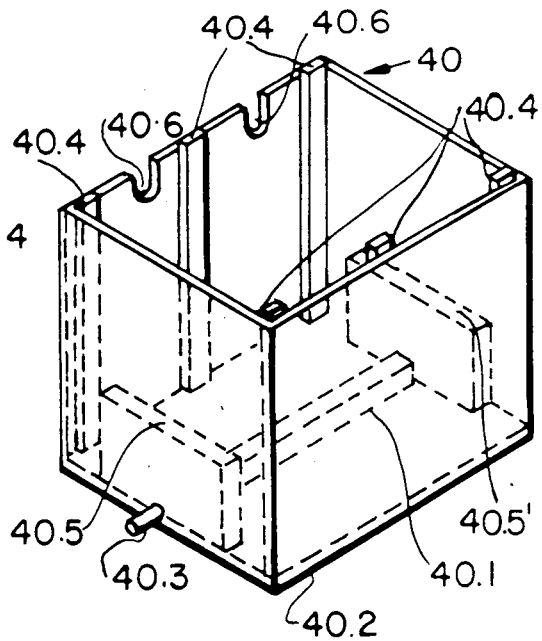

In FIG. 12, a cross-member bar 40.1 is affixed to the bottom sheet 40.2 of the bottom buffer chamber member 40. To the top of said cross-member bar 40.1 is affixed a platinum wire (not shown) along its length, said wire being connected to an electrical connection point 40.3. The deflector 29, for deflecting gas bubbles evolved at the electrode, is not shown. Again the spacer strips 40.4 and side members 40.5 and 40.5' serve to assist in aligning the member with the cooling chamber member during and in assembly. Indentations 40.6 and 40.6' are provided in the appropriate wall, to accommodate the cooling liquid inlet and outlet ports 32 and 32'.

In FIG. 13 the numeral 26 indicates a vertical electrophoresis apparatus, with the lid member 34 and bottom buffer member 40 removed, and the multi-gel cartridge unit 12 and sample comb 25 in position, the assembly being placed such as to rest via a rubber sheet 42 and a polymethylmethacrylate member 44 (see FIG. 14) on a casting stand 46. The rubber sheet 42 is provided with a clot which encloses the bottom of the multi gel cartridge unit 12, while the member 44 is provided with a circular hole of equal or slightly smaller diameter than the diameter of the rim of a funnel 48, suspended in a hole 46.1 (FIG. 14) provided in the stand 46. A sealing rubber band 50, moulded such as to contain a groove to enable it to fit tightly on to the rim of funnel 48, is used to form a watertight seal between the funnel 48 and the member 44. Two reservoirs 52 and 54 are supported on a retort stand 56 and are connected via a three-way tap 58 and flexible tubing 60 to the bottom of funnel 48.

To cast a multi-gel slab gel, the required solution (A) containing the necessary ingredients for the formation of the multi-gel (for example a polyacrylamide gel) is measured out and placed in one reservoir 52, while displacement solution (e.g. a 30% sucrose solution) is placed in the second reservoir 54. All of solution A is run into the funnel 48, followed by running in of the displacement solution, allowing solution A slowly to ascend up the multi-gel cartridge unit 12 until the teeth of sample comb 25 are partially or wholly covered. Some water or buffer solution is now carefully placed on to the exposed surface of the acrylamide solution and time allowed for the acrylamide to gel. The sample comb is then removed, and the plunger rod 16'.3 withdrawn from the side stop 16' (see FIG. 2), to allow air to enter into the bottom section of the multi-gel cartridge unit while the displacement solution is drained.

Assembly of the vertical electrophoresis apparatus is now completed as follows:

The plunger rod 16'.3 is first pushed down, making use of vaseline or silicone grease to ensure a watertight fit. The bottom buffer chamber 40 is then partially filled with buffer solution and the assembly of cooling chamber member, top buffer camber member and multi-gel cartridge unit, with the multi-gel slab gel cast therein, fitted into position. It should be ensured that there is contact of the bottom of the multi-gel slab gel with the buffer solution. (Excess buffer solution is displaced upwards between the cooling chamber member and the walls of the bottom buffer chamber member—see FIG. 8.) A thin layer of buffer solution (for example about 10 to 20 mm deep) is placed on the top of the multi-gel slab gel, to at least fill and just submerge the sample wells. The samples (for example mixed with a 10% sucrose solution, to give them a relatively high density) are now carefully dispensed into the sample wells; the top buffer chamber member is topped up with buffer solution, the lid member is fitted on, and the electrodes connected to the high-voltage supply unit, and the run completed. (It may be noted that the circulation of cooling liquid (or for that matter any temperature controlled circulating liquid) may already be started while the multi-gel is being poured, thus permitting the polymerisation of the gel to take place under temperature controlled conditions.)

At the end of the run, the cooling liquid circulation is stopped, buffer solution from the top buffer chamber member is siphoned off and the multi-gel cartridge unit, with multi-gel slab gel, removed and placed on a firm surface with the glass sheet to which the spacer stops had been secured at the bottom. A scalpel blade is used to cut through the tape, to free the side stops and topmost glass sheet. By means of the scalpel, the stack of micro gels is freed by cutting through the plastic layers along the spacer sheets on both sides. Individual micro gels may now be separated by inserting the tip of the scalpel under each divider sheet in turn, and peeling off the divider sheet plus micro-gel adhering to its top surface. (Even very thin microgels may be readily manipulated in this way.)

In FIG. 15, a horizontal electrophoresis apparatus 64 is shown to comprise a base plate 66 of glass, on to which are mounted two buffer chambers 68 and 68', secured to the base plate 66 by silicone glue, and constructed of polymethylmethacrylate members similarly glued together. The inside walls 68.1 and 68'.1 are each provided with a recess, which together with the base plate 66 forms a slot 68.1.1 nd 68'.1.1. Also provided in each of the inside walls 68.1 and 68'.1 of the buffer chambers 68 and 68' are further recesses 68.1.2 and 68.1.2', 68'.1.2 and 68'.1.2', to function as "stops" for the spacer sheets 70 and 70' (equivalent to 8 and 8' in FIG. 1), here not yet tacked in position with double-sided adhesive tape (not shown).

FIG. 16 shows the stacks of spacer sheets 70 and 70' in position, with a plurality of divider sheets (only the top one 10 of which is shown) spanned therebetween. The multi-gel 72 of polyacrylamide has been cast in a multi-gel casting unit, with slots towards its one end. Also shown is a plurality of sample wells 72.1 in the multi-gel 72 produced by means of a sample comb (see FIG. 17). (The multi-gel 72 spans approximately the distance between 72.2 and 72.3.)

The sample comb 74 (FIG. 17) for use together with a multi-gel casting unit in a horizontal electrophoresis apparatus 64 comprises a sheet 74.1 of polymethylmethacrylate, with a row of teeth 74.2 affixed at right angles to the sheets 74.1.

In FIG. 18a, the wedge-shaped spacers 6, 6', 6" and 6''' which are glued to the base plate (not shown) are used to "stop" the spacer sheets 8 and 8'. Also shown is a divider sheet 10 spanned across the single spacer sheets 8 and 8' shown. In FIG. 18b the spacer stops 6, 6', 6" and 6''' comprise two strips of polymethylmethacrylate sheeting on each side protrudingly embedded in the inside walls 68.1 and 68'.1 of the buffer chamber 68 and 68'—they may also be removably affixed—whereas in FIG. 18c the spacer "stops" comprise recesses 68.2, 68.2', 68'.1 and 68'.2' provided in the corners of the buffer chamber walls as shown. In the latter case the spacer sheets 8 and 8' need to be somewhat longer than in the embodiments shown in FIGS. 18a and 18b.

In FIG. 19, a cooling means 76 comprise a 2 mm thick metal plate 76.1, with a coil 76.2 of metal tubing affixed (e.g. by spot-welding) thereto. Cooling is effected by circulating for example tap water through coil 76.2.

FIG. 20 shows the base plate 66 resting on a bottom cooling plate 76 comprising a metal plate 76.1 and the coils 76.2 of metal tubing. A top cooling plate 76', comprising a corresponding metal plate 76'.1 and coils 76'.2 of a metal cooling tube, rests on top of a top glass plate 66', which in turn is placed on top of the multi-gel casting unit. Each buffer chamber 68 and 68' is covered with a loose-fitting cover plate 78 and 78' provided with a cross-member 78.1 and 78'.1 to which is attached a platinum wire electrode 78.1.1 and 78'.1.1 connected to an electrical connection point 78.1.2 and 78'.1.2. Holes are optionally provided in the cover plates 78 and 78', to permit easy escape of gases generated at the electrodes during an electrophoresis run.

In FIG. 21, an embodiment of a sample comb 74 for use in a horizontal electrophoresis apparatus is shown in which the teeth 74.2 are removably affixed to the sample comb plate 74.1 by means of a rubber layer 74.3 cast in a slot in the sample comb plate 74.1. Two of the teeth have been removed from the comb 74 as shown. To facilitate sealing off of the slot in the top glass plate of the split multi-gel cartridge unit during casting of the multi-gel slab gel, a 1 mm thick sheet of rubber (not shown) with a rectangular hole therein large enough to enclose the row of teeth of the sample comb 74, and of overall dimensions substantially the same as those of the top plate of the split multi-gel cartridge unit, is placed in between the sample comb and the top plate during casting of the multi-gel slab gel.

FIG. 22 shows the use of a split multi-gel cartridge unit with multi-gel slab gel cast therein. Here the top plate is provided in two equal parts, to provide a slot 73 in which the sample wells 73.1 are provided approximately along a central dividing line in the multi-gel slab gel. The thin divider sheets are also provided in two sets 10 and 10'. This arrangement allows detection in the zymogram of analytes which during the electrophoresis run have migrated both towards the cathode and towards the anode.

FIG. 23 illustrates approximately one half of a horizontal electrophoresis apparatus which makes us of two buffer chambers 68 and 80 used in tandem on the side shown, the latter 80 being regarded as an auxiliary buffer chamber. The pair of buffer chambers are electrically connected by means of a wick 82. The cross bars 68.3 and 80.3 assist in holding the wick 82 in position. Also shown is a cover lid 78 with cross member 78.1 with affixed electrode 78.1.1 in a partially exploded view. The numeral 84 indicates part of the split multi-gel cartridge unit with associated multi-gel slab gel. The numeral 66 indicates the extended base plate.

FIG. 24 shows a horizontal electrophoresis apparatus adapted for use with a multi-gel cartridge assembly unit. The buffer chambers 68 and 68' are provided with their own sub base plates 68.5 and 68'.5, of which parts have been cut away, indicated by 68.4 and 68'.4, to accommodate the sub base plate 88 of the multi-gel cartridge assembly unit.

In FIG. 25 the split multi-gel cartridge unit 80 with a multi-gel slab gel provided therein is suspended between the edges of two buffer chambers 68 and 68'. Wicks 90 and 90' are used to provide electrical contact between the buffer solutions 68.6 and 68'.6 during electrophoresis. This illustration represents horizontal electrophoresis in the conventional manner but using a split multi-gel cartridge unit with a multi-gel slab gel provided therein.

Cooling may be effected by one or two cooling means (not shown) placed such as to make contact with the top and/or the bottom surfaces of the split multi-gel cartridge unit 80. Covering lids (not shown) with electrodes provided therein are placed on the buffer chambers such that electrodes are immersed in the buffer solutions 68.6 and 68'.6.

In FIG. 28 the slot 68.1.2 provided in the inside wall 68.1 of a buffer chamber 68, is contiguous with the bottom extended base plate 66 (not shown) and lined with a layer of rubber 68.1.3, which is suitably contoured to accommodate a (split) multi-gel cartridge unit (not shown).

In FIG. 26 the tapered slot 68'.1.2 to accommodate a (split) multi-gel cartridge unit together with a flexible seal (not shown) is provided about two-thirds up the height of the inner wall 68.1 of the buffer chamber 68. This embodiment makes for greater manipulative convenience in fitting the (split) multi-gel cartridge unit into the slot via the flexible seal. The buffer chamber 68 is shown to be subdivided into two separate compartments by means of a sheet 68.7 of appropriate size. The barrier 68.7 allows the use of a single buffer chamber or two buffer chambers in tandem (e.g. by providing electrical contact by means of a wick or salt bridge). 68.8 and 68'.8 are top partial members provided for facilitating handling of the buffer chamber as well as for supporting the lid when placed in position.

An additional flexible seal entirely closed off at its narrower end (and designated a "jacket seal") may additionally be provided. By the use of this jacket seal a multi-gel casting unit may be placed with one of its open ends to fit sealingly in the slot 68.1.2 of this buffer chamber, and while the buffer chamber plus split multi-gel cartridge unit fitted therein is positioned in a vertical configuration, with the sample comb 74 (FIG. 21) fitted in position sealingly by means of a rubber sheet with a rectangular hole provided therein and adhesive tape, a gel may be cast in the split multi-gel cartridge unit. Alternatively, by the use of the appropriate sample comb 25 (FIG. 6) a multi-gel slab gel, for use in a vertical electrophoresis apparatus (FIG. 7), may also be conveniently cast in a multi-gel cartridge unit (FIG. 2) using the jacket seal.

FIG. 27 shows a preferred embodiment of a horizontal electrophoresis apparatus in accordance with the invention in use: the (split) multi-gel cartridge unit 80 plus multi-gel slab gel cast therein is in direct electrical contact with the buffer solutions, having been fitted into slots 68.1.2 and 68'.1.2 in the inner walls 68.1 and 68'.1 of the buffer chambers 68 and 68' (as in FIG. 27) by means of flexible seals. A cooling means 76 is provided as indicated.

Although only certain embodiments of the invention have been described above, it will be readily apparent to those skilled in the art that the scope of the invention is not to be considered limited by these embodiments, and that there are numerous variants and modifications of the invention possible which fall within scope of the invention as claimed.

The entire texts of all applications, patents and publications, if any, cited above and below, and of corresponding application 88/2019 filed Mar. 22, 1988 in the Republic of South Africa, are hereby incorporated by reference.

We claim:

1. A multi-gel slab gel for use in gel electrophoresis comprising a plurality of wafer-like layers of gel, said layers having thicknesses in the range of about 0.1 to 8 mm and being separated by one more divider webs.

2. A gel as claimed in claim 1, wherein the divider webs each consist of plastic sheet of from 6 to 250 μm in thickness.

3. A gel as claimed in claim 1, in which the gel comprises polyacrylamide, agarose or starch.

4. A gel as claimed in claim 1, assembled to form a gel electrophoresis apparatus, including:
   (1) a multiple gel cartridge unit, wherein the multi-gel slab gel is accommodated;
   (2) sample introduction formations for introducing into the gel samples to be subjected to electrophoresis;
   (3) buffer chambers at opposite ends of the cartridge unit in electrical contact with the gel for containing a buffer in contact with the gel and connected to electrical terminals for applying, via buffer contained in the buffer chambers, a potential difference between the opposite ends of the gel; and
   (4) cooling means for the multi-gel slab.

5. A gel electrophoresis apparatus, comprising
   (1) a multi-gel cartridge unit wherein is accommodated or which is adapted to accommodate a multi-gel slab gel as claimed in claim 1,
   (2) sample introduction formations for introducing into the gel samples to be subjected to electrophoresis;
   (3) buffer chambers at opposite ends of the cartridge unit in electrical contact with the gel for containing a buffer in contact with the gel and connected to electrical terminals for applying, via buffer contained in the buffer chambers, a potential difference between the opposite ends of the gel; and
   (4) cooling means for the multi-gel slab.

6. An apparatus as claimed in claim 5, wherein the cartridge unit is disposed vertically.

7. A vertical electrophoresis apparatus as claimed in claim 6, comprising a top buffer chamber member having a bottom wall provided with an aperture which establishes a sealing relationship with the upper end of the multi-gel cartridge unit, containing or adapted to receive the multi-gel slab gel cast therein in communication with the interior of the top buffer chamber member; a bottom buffer chamber which via an aperture in a top partition on the bottom buffer chamber member establishes a sealing relationship with the bottom end of the multi-gel cartridge unit and provides communication between the interiors of the cartridge and the bottom buffer chamber member.

8. An apparatus as claimed in claim 7, comprising a cooling chamber member adapted to enclose the multi-gel cartridge unit and to provide a coolant jacket therefor.

9. An apparatus as claimed in claim 8, wherein the buffer chamber members, the multi-gel cartridge unit and the cooling chamber member constitute separate modules adapted to be assembled in sealing relationship with one another.

10. An apparatus as claimed in claim 9, wherein the said apertures of the top and bottom buffer chambers are tapered to receive the opposite ends of the multi-gel cartridge unit in sealing relationship.

11. An apparatus as claimed in claim 9, wherein the top partition on the bottom chamber member is part of the cooling chamber member.

12. An apparatus as claimed in claim 7, wherein the walls of the bottom buffer chamber member extend above the level of the said top partition to provide a cavity for a head of buffer liquid.

13. An apparatus as claimed in claim 6 in combination with a casting device for use in casting the multi-gel slab gel into the multi-gel cartridge unit, the casting device being adapted to fit underneath the electrophoresis apparatus including the empty multi-gel cartridge unit, after the removal of that buffer chamber from the bottom end of the cartridge unit, and comprising connector means for connecting in sealing relationship to the said bottom end a feed duct leading from reservoir means for supplying gel forming solution to the cartridge unit to fill the same from the bottom upwards with gel forming solution.

14. An apparatus as claimed in claim 13, including a sample comb comprising a serrated edge or a set of teeth, adapted to be fitted removably into the top of the cartridge unit during casting of the gel to serve as a mold for a plurality of sample wells in the top of the multi-gel slab gel.

15. An apparatus as claimed in claim 5, wherein the cartridge unit is horizontally disposed.

16. A horizontal electrophoresis apparatus as claimed in claim 15, which is additionally provided with a pair of auxiliary buffer chambers to be connected in an "in tandem" arrangement with the main buffer chambers by wicks or salt bridges.

17. A horizontal electrophoresis apparatus as claimed in claim 15, wherein the buffer chambers are removably fitted in sealing relationship to opposite ends of the cartridge unit.

18. A horizontal electrophoresis apparatus as claimed in claim 17, in which slots provided in the inner walls of the buffer chambers are adapted by suitable contouring such that the slots together with the contiguous surface of the extended base plate are capable of receiving in a watertight fit the ends of a multi-gel cartridge unit.

19. A horizontal electrophoresis apparatus as claimed in claim 15, wherein the cartridge unit comprises
    a sub-base plate and a top plate of electrically non-conducting material, connected by
    two electrically non-conducting elongate side-stops, separating the base plate and top plate in sealing relationship therewith, and
    a cooling means underneath the sub-base plate and optionally also on top of the top plate.

20. A horizontal electrophoresis apparatus as claimed in claim 19, in which the bottom cooling means and/or top cooling means comprise a solid metal plate, optionally provided with a metal tube, optionally formed into coils, affixed thereto through which cooling liquid may be circulated for carrying away the heat generated in the apparatus during an electrophoresis run.

21. Apparatus as claimed in claim 15, wherein the sub-base plate is extended to form a bottom wall of the buffer chambers.

22. Apparatus as claimed in claim 21, in which the buffer chambers are permanently affixed to the sub-base plate.

23. Apparatus as claimed in claim 21, wherein either or each of the buffer chambers is movable in relation to the base plate.

24. Apparatus as claimed in claim 23, wherein the spacing between the buffer chambers is adjustable to accommodate different lengths of cartridge unit.

25. A horizontal electrophoresis apparatus as claimed in claim 23, in which the buffer chambers are adapted to be slidingly affixed to the extended base plate, optionally with the outside walls of the buffer chambers extending around the extended base plate to provide guiding grooves in which the buffer chambers may slide.

26. Apparatus as claimed in claim 15, wherein the top plate of the cartridge unit comprises one or more gaps or apertures for sample introduction therethrough into sample wells in the multi-gel slab gel underneath the top plate.

27. Apparatus as claimed in claim 26 in combination with a sample comb or combs adapted to be inserted in the gaps or apertures during casting of the multi-gel slab gel, serving as a mold for the sample wells.

28. A horizontal electrophoresis apparatus as claimed in claim 27, in which the sample comb comprises a length of a sheet with affixed at right angles thereto a row of teeth or a serrated strip adapted to produce in use a plurality of sample wells in a multi-gel slab gel cast in a multi-gel casting unit when the gel mixture has set after casting.

29. A horizontal electrophoresis apparats as claimed in claim 28, in which individual teeth of the sample comb are fitted slidingly and removably into slots, optionally rubber-lined, such that the teeth may be manipulated individually.

30. A multi-gel cartridge unit for casting therein or containing cast therein a multi-gel slab gel as claimed in claim 1, comprising
    a sub-base plate and a top plate of electrically non-conducting material, connected by
    elongate electrically non-conducting side stops separating the two plates along two opposite sides in sealing relationship and providing open end therebetween, and one or more dividers webs held taut in a fixed position to divide the space between the plates into a plurality of wafer-like cavities occupied or adapted to be occupied by said layers of gel.

31. A multi-gel cartridge unit as claimed in claim 30, in which at least one of said side-stops are provided with a cylindrical space with a fitted plunger rod.

32. A unit as claimed in claim 30, comprising inside stop formations for positioning spacer means holding in place the one or more divider webs.

33. A unit as claimed in claim 30, wherein the top plate is interrupted along one or more lines transversely between the sides closed by the side stops by aperture or gap means providing access to sample wells in the gel, and each divider web is interrupted by apertures or gap means in positions matching the aforesaid aperture or gap means.

34. A multi-gel casting unit as claimed in claim 33, in which the side stops comprise at least on one side, a first tube, with fitted plunger rod, and optionally on the other side a rod, both tubes or tube and rod being provided with larger half-tubes, the inner diameter of which is such that the first tube or rod fits snugly therein, the side stops being affixed in position to the sub base plate (i) and optionally also the top plate (1).

35. A multi-gel casting unit as claimed in claim 33, together with a prepacked multi-gel, as claimed in claim 1, provided therein.

36. A unit as claimed in claim 33, wherein the aperture or gap means is at a distance of about 10 to 20 mm from one of the open ends of the unit.

37. A unit as claimed in claim 33 in which the top plate is divided to provide a gap in the desired position between the open ends of the unit.

38. A multi-gel slab gel for use in electrophoresis comprising a plurality of wafer-like layers of gel separated by one or more divider webs, including a divider means, comprising a plurality of spacer strips, provided in the form of two stacks, each spacer strip in one stack being of substantially equal thickness to that of the corresponding spacer strip in the other stack, and with divider webs affixed between each pair of successive spacer strips in one stack and the corresponding pair of spacer strips in the other stack.

39. A gel as claimed in claim 38, in which the divider webs comprise polyethylene, polyester or any other suitable thin plastic sheeting material, including heat-shrink sheeting material.

40. A gel as claimed in claim 38, in which the divider webs are secured to the spacer strips, and the bottom spacer strips to a base plate by means of double-sided adhesive tape, by gluing, by suitable heat treatment or by means of ultrasonics.

41. A gel as claimed in claim 38, in which the set of divider webs are split in two or more sets by suitably punching out a gap or gaps.

42. A gel as claimed in claim 38, in which one or more rows of holes are punched into the set of divider set webs.

43. A gel as claimed in claim 38, in which the spacer strips are all of substantially equal thickness.

44. A gel as claimed in claim 38, in which the spacer strips are of variable thickness, with the proviso that any spacer strip in one stack is substantially of the same thickness as the corresponding spacer strip in the other stack.

45. A gel as claimed in claim 38 in a cartridge form comprising
(a) a sub-base plate of non-conducting material,
(b) means for locating the divider means in relation to the sub-base plate; and
(c) a top plate of non-conducting material.

46. A gel as claimed in claim 45, wherein the cartridge is closed and sealed along two opposite sides by two non-conducting elongate side-stops separating the base plate and top plate.

47. A gel as claimed in claim 46, in which either or both of the side-stops enclose a cylindrical air vent cavity with a plunger rod fitted therein.

48. A gel as claimed in claim 45, wherein the top plate is divided transversely by one or more sample introduction gaps or openings.

49. A gel as claimed in claim 45, wherein sample introduction wells are provided at an end of the gel.

50. A replaceable, cast multi-gel slab gel adapted for installation in a gel electrophoresis apparatus in the form of a slab, comprising a plurality of wafer-like layers of gel, said layers having thicknesses in the range of about 0.1 to about 8 mm and being separated by one or more divider webs.

51. A gel as claimed in claim 50, wherein the divider webs each consist of plastic sheet of from 6 to 250 $\mu$m in thickness.

52. A gel as claimed in claim 50, made up in the form of a replaceable and disposable cartridge.

* * * * *